United States Patent [19]

Ishikawa et al.

[11] 3,969,428

[45] July 13, 1976

[54] PROCESS FOR THE PRODUCTION OF CONJUGATED DIOLEFINS

[75] Inventors: Toshio Ishikawa; Takashi Hayakawa, both of Tokyo; Tsutomu Nishimura, Koganei; Michio Araki, Mitaka; Katsuomi Takehira, Tokyo, all of Japan

[73] Assignee: Agency of Industrial Science & Technology, Tokyo, Japan

[22] Filed: Oct. 11, 1974

[21] Appl. No.: 513,959

[30] Foreign Application Priority Data

Nov. 5, 1973  Japan.............................. 48-124139

[52] U.S. Cl. .............................. 260/680 E; 252/468
[51] Int. Cl.² ........................................... C07C 5/48
[58] Field of Search ................................ 260/680 E

[56] References Cited

UNITED STATES PATENTS

| | | |
|---|---|---|
| 3,159,688 | 12/1964 | Jennings et al................... 260/680 E |
| 3,480,564 | 11/1969 | O'Brien et al.................... 260/680 E |
| 3,642,930 | 2/1972 | Grasselli et al.................. 260/680 E |
| 3,666,822 | 5/1972 | Grasselli et al.................. 260/680 E |
| 3,821,324 | 6/1974 | Bertus ............................. 260/680 E |
| 3,862,256 | 1/1975 | Isailingold et al............... 260/680 E |

*Primary Examiner*—Paul M. Coughlan, Jr.

[57] ABSTRACT

A process for the production of conjugated diolefins having 4–6 carbon atoms from the corresponding monoolefins according to the oxidative dehydrogenation process wherein oxides of molybdenum, arsenic and an alkaline earth metal are used as catalyst. The use of this catalyst enables the production of conjugated diolefins in a high yield.

5 Claims, No Drawings

PROCESS FOR THE PRODUCTION OF CONJUGATED DIOLEFINS

BACKGROUND OF THE INVENTION

This invention relates to a process for the production of conjugated diolefins having 4–6 carbon atoms. More particularly, this invention relates to a process for the production of conjugated diolefins having 4–6 carbon atoms from the corresponding monoolefins by a vapor phase reaction conducted at a high temperature in the presence of oxygen wherein a specific catalyst is used to obtain the end product in a high yield.

A process for the vapor phase dehydrogenation of monoolefins conducted at a high temperature in the presence of oxygen while allowing the oxygen to participate in the reaction is already known as a means for producing diolefins. This process is known as the so-called "oxidative dehydrogenation process" and is characterized in that it is advantageous with respect to the thermal energy of the reaction as compared with the direct dehydrogenation process wherein monoolefins are heated in the absence of oxygen with a heating medium such as steam. However, such oxidative dehydrogenation is an oxidation reaction and as such, has disadvantages in that it permits the formation of a number of by-products and fails to produce the desired diolefins in a high yield.

In general, the oxidative dehydrogenation reaction is carried out in the presence of a catalyst to overcome the aforementioned disadvantages or in other words, to enhance the reaction rate and the yield of the product. Examples of catalysts proposed for said oxidation dehydrogenation include a catalyst comprising oxides of tungsten and cobalt or oxides of molybdenum and cobalt (Japanese Patent Publn. No. 27049/1965), a catalyst comprising oxides of molybdenum, bismuth and arsenic (British Patent 906,215) and a catalyst comprising oxides of (i) tellurium and (ii) iron, tin or titanium (Japanese Patent Publn. No. 5723/1968). However, all of these hitherto proposed catalysts are not satisfactory in their activity and selectivity so that the yield of conjugated diolefins achieved is not high. Thus, there is still a great demand for development of a new type catalyst which can overcome these disadvantages found in the conventional catalysts.

BRIEF SUMMARY OF THE INVENTION

It is an object of this invention to provide an improved process for the production of conjugated diolefins having 4–6 carbon atoms by oxidatively dehydrogenating the corresponding monoolefins.

It is another object of this invention to provide a process for the production of conjugated diolefins having 4–6 carbon atoms by oxidatively dehydrogenating the corresponding monoolefins wherein a catalyst possessing high activity and selectivity is used to produce the diolefins in an extremely high yield.

Other objects, features and advantages of this invention will become apparent more fully as the description proceeds.

DETAILED DESCRIPTION OF THE INVENTION

As the result of much research done on the processes for the production of conjugated diolefins by the oxidative dehydrogenation process, it has now been found that a combination of oxides of molybdenum, arsenic and an alkaline earth metal possesses high catalytic activity and selectivity for such dehydrogenation reaction and enables one to produce conjugated diolefins in an extremely high yield.

In accordance with this invention, therefore, there is provided a process for the production of conjugated diolefins having 4–6 carbon atoms from the corresponding monoolefins which comprises oxidatively dehydrating said monoolefins having 4–6 carbon atoms in the vapor phase in the presence of molecular oxygen at a temperature of 300°–600°C, characterized in that said monoolefins are brought into contact with a catalyst comprising oxides of molybdenum, arsenic and an alkaline earth metal.

Illustrative of the starting olefins used in the process of this invention are monoolefins with 4–6 carbon atoms such as 1-butene, 2-methyl-1-butene, 1-pentene, 2-pentene, 2-methyl-1-pentene, 1 hexene and 3-hexene. These monoolefins are dehydrogenated to give butadiene, isoprene, pentadiene, 2-methyl-1-pentadiene, hexadiene and the like corresponding conjugated diolefins. As paraffinic hydrocarbons are not affected by the oxidative dehydrogenation, these monoolefins may be employed in the form of a mixture with paraffinic hydrocarbons. The starting hydrocarbon suitable for the production of butadiene is a $C_4$ fraction obtained by refining petroleum, which contains various n-butenes and butanes.

The oxide catalysts used for the process of this invention are represented by the following empirical formula:

$$Mo_aMe_bAs_cO_d$$

wherein Me stands for an alkaline earth metal selected from among Mg, Ca, Sr and Ba, $a$ is 1, $b$ is 0.1–1, $c$ is 0.1–1 and $d$ stands for the number of oxygen atoms which satisfy the valence of the metals in oxidized state.

The catalyst of this invention may be used alone but, if necessary, it may be carried on a conventional porous support such as silica, alumina or silica-alumina.

The catalyst of this invention is prepared by mixing molybdic acid, pyroarsenic acid and an oxide or hydroxide of an alkaline earth metal in a proportion necessary to satisfy the above empirical formula, and baking the mixture in the air at a temperature of 200°–600°C, preferably at 450°–550°C. The catalyst carried on a support can be prepared by adding the support to a mixture of the catalyst components. In the catalyst carried on a support, the catalyst components are contained in an amount of 20–60% by weight, preferably 40–50% by weight.

In the catalyst of this invention, the arsenic component is especially important in respect of selectivity of the catalytic action. A catalyst free of the arsenic component, i.e. a catalyst comprising oxides of molybdenum and an alkaline earth metal also exhibits a high catalytic action for oxidative dehydrogenation of monoolefins. However, such catalyst exhibits a high activity also for isomerization, thus resulting in lowering of selectivity to the end products. This disadvantage is significantly overcome by addition of the arsenic component.

The process of this invention is carried out by bringing the starting monoolefins and molecular oxygen in 0.5–2 molar proportion, preferably 1–1.5 molar proportion to the monoolefins into contact with the catalyst system of this invention for 0.5–20 seconds, preferably 1–10 seconds at a reaction temperature of 300°–600°C, preferably 400°–500°C. Air is a preferable source of the molecular oxygen and, in this case, the air is used in a volume of 1–9 times as much as the starting monoolefins.

The effect of the catalyst system of this invention is indeed remarkable in that in the oxidative dehydrogenation reaction of the monoolefins to the corresponding diolefins, both conversion rate and selectivity are significantly enhanced when compared with the known prior art processes.

This invention will now be explained in more detail by way of examples. However, it is to be construed that the scope of this invention is not limited by these examples.

EXAMPLE 1

18.0 Grams of molybdic acid [$(H_2MoO_4)\cdot H_2O$] (Mo content: 0.1 g - atom), 13.4 g of pyroarsenic acid [$H_4As_2O_7$] (As content: 0.1 g - atom) and 31.6 g of barium hydroxide [$Ba(OH)_2\cdot 8H_2O$] (Ba content: 0.1 g - atom) were placed in an evaporating dish in a water bath. A small amount of water was added to this mixture and the whole was evaporated until dryness while kneading the mixture with a pestle. A small amount of water was added to the dried residue and the mixture was again evaporated until dryness under agitation. The dried residue was then gradually heated in an electric furnace up to 500°C and baked for 3 hours at this temperature. The baked product was then pulverized and particles having a particle size of 30–40 mesh were collected to obtain a Mo-Ba-As catalyst.

In a stainless steel reaction tube of 10 mm in diameter and 400 mm in length were placed 3.5 g (volume: 3 cc) of the catalyst obtained by the aforesaid treatment. 1-Butene was then passed, together with air, through the reaction tube at a reaction temperature of 490°C. In this case, the contact time was 2.7 seconds and the ratio by volume of the butene-1 to the air was 17/83. In this experiment, 46.9% of butene-1 was reacted and 91.5% of the reacted butene-1 was converted into butadiene.

For the purpose of comparison, a Mo-Ba catalyst was prepared from 18 g of molybdic acid and 31.6 g of barium hydroxide according to the same treatment as described above. Using this Mo-Ba catalyst, an oxidative dehydrogenation reaction was carried in a manner similar to that described above except that the contact time and the reaction temperature were 0.9 seconds and 470°C, respectively. As a result of this experiment, it was found that 20.7% of butene-1 was reacted and 74.5% of the reacted butene-1 was converted into butadiene.

EXAMPLE 2

A Mo-Ca-As catalyst was prepared from 18 g of molybdic acid, 7.4 g of calcium hydroxide [$Ca(OH)_2$] (Ca content: 0.1 g - atom) and 13.4 g of pyroarsenic acid according to a method similar to that described in Example 1. Using this Mo-Ca-As catalyst, an oxidative dehydrogenation reaction was carried out in a manner similar to that described in Example 1 except that the contact time and the reaction temperature were 0.9 second and 470°C, respectively. As a result of this experiment, it was found that 40.5% of butene-1 was reacted and 88.1% of the reacted butene-1 was converted into butadiene.

EXAMPLE 3

A Mo-Sr-As catalyst was prepared from 18 g of molybdic acid, 26.6 g of strontium hydroxide [$Sr(OH)_2\cdot 8H_2O$] (Sr content: 0.1 g - atom) and 13.4 g of pyroarsenic acid according to a method similar to that described in Example 1. Using this catalyst, an oxidative dehydrogenation reaction was carried out in a manner analogous to that described in Example 2. As a result of this experiment, it was found that 39.4% of butene-1 was reacted and 87.1% of the reacted butene-1 was converted into butadiene.

EXAMPLE 4

A Mo-Mg-As catalyst was prepared from 18 g of molybdic acid, 13.4 g of pyroarsenic acid and 4.0 g of magnesium oxide [MgO] (Mg content: 0.1 g - atom) according to a method similar to that described in Example 1. Using this catalyst, an oxidative dehydrogenation reaction was carried out in a manner analogous to that described in Example 2. As a result of this experiment, it was found that 39.4% of butene-1 was reacted and 87.1% of the reacted butene was converted into butadiene.

EXAMPLE 5

An oxidative dehydrogenation was carried out in a manner analogous to that described in Example 2 except that a $C_4$ fraction containing 0.25% of carbon dioxide, 3.93% of iso-butane, 17.13% of n-butane, 59.92% of butene-1, 18.2% of butene-2 and 0.55% of butadiene was used as the starting monoolefins. As a result of the experiment, it was found that 17.6% of the butenes were reacted and 87.5% of the reacted butenes were converted into butadiene.

Obviously many modifications and variations of this invention are possible in the light of the above teachings. It is therefore to be understood that within the scope of the appended claims, the invention may be practiced otherwise than as specifically described.

What is claimed is:

1. A process for the production of conjugated diolefins having 4–6 carbon atoms from the corresponding monoolefins which comprises oxidatively dehydrogenating monoolefins having 4–6 carbon atoms in the vapor phase in the presence of molecular oxygen at a temperature of 300°–600°C, characterized in that said monoolefins are brought into contact with a catalyst consisting essentially of oxides of molybdenum, arsenic and an alkaline earth metal selected from the group consisting of magnesium, calcium, strontium and barium and represented by the empirical formula:

$$Mo_aMe_bAs_cO_d$$

wherein Me stands for said alkaline earth metal, $a$ is 1, $b$ is 0.1–1, $c$ is 0.1–1 and $d$ stands for the number of oxygen atoms which satisfy the valence of the metals in the oxidized state.

2. A process according to claim 1 wherein said catalyst has been prepared by baking a mixture of molybdic acid, pyroarsenic acid and an oxide or hydroxide of an alkaline earth metal at a temperature of 200°–600°C in the air.

3. A process according to claim 1 wherein said catalyst is carried on a porous support.

4. A process according to claim 1 wherein said monoolefins are in the form of a mixture with paraffinic hydrocarbons.

5. A process according to claim 1 wherein said monoolefins are a $C_4$ fraction obtained by refining petroleum.

* * * * *